United States Patent
Hayashi et al.

(10) Patent No.: US 7,458,974 B1
(45) Date of Patent: Dec. 2, 2008

(54) APPARATUS AND METHOD FOR ELECTRICALLY INDUCED THROMBOSIS

(75) Inventors: Reid K. Hayashi, Palo Alto, CA (US); Mark T. LeMere, San Francisco, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 146 days.

(21) Appl. No.: 10/282,608

(22) Filed: Oct. 28, 2002

Related U.S. Application Data

(63) Continuation of application No. 09/624,924, filed on Jul. 25, 2000, now abandoned.

(51) Int. Cl.
*A61B 18/12* (2006.01)
(52) U.S. Cl. ............ 606/50; 606/41; 606/49
(58) Field of Classification Search .......... 606/27–52
See application file for complete search history.

(56) References Cited

U.S. PATENT DOCUMENTS

| | | | | |
|---|---|---|---|---|
| 4,522,205 | A | * | 6/1985 | Taylor et al. ............ 606/49 |
| 5,007,908 | A | * | 4/1991 | Rydell ............ 606/47 |
| RE33,925 | E | * | 5/1992 | Bales et al. ............ 606/48 |
| 5,330,470 | A | * | 7/1994 | Hagen ............ 606/42 |
| 5,336,222 | A | * | 8/1994 | Durgin et al. ............ 606/50 |
| 5,429,636 | A | * | 7/1995 | Shikhman et al. ............ 606/41 |
| 5,447,533 | A | * | 9/1995 | Vachon et al. ............ 607/120 |
| 5,514,130 | A | * | 5/1996 | Baker ............ 606/41 |
| 5,800,484 | A | * | 9/1998 | Gough et al. ............ 607/104 |
| 5,830,209 | A | * | 11/1998 | Savage et al. ............ 606/15 |
| 5,868,740 | A | * | 2/1999 | LeVeen et al. ............ 606/41 |
| 6,027,501 | A | * | 2/2000 | Goble et al. ............ 606/41 |
| 6,066,138 | A | * | 5/2000 | Sheffer et al. ............ 606/49 |
| 6,106,524 | A | * | 8/2000 | Eggers et al. ............ 606/50 |
| 6,193,717 | B1 | * | 2/2001 | Ouchi ............ 606/49 |

OTHER PUBLICATIONS

Gugliemi, G. M.D., et al., "Electrothrombosis of *Saccular aneruysms* Via Endovascular Approach," Part I: Electrochemical Basis, Technique, and Experimental Results, J. Neurosurg. vol. 75, Jul. 1991, pp. 1-7.

Gugliemi, G. M.D., et al., "Electrothrombosis of *Saccular aneruysms* Via Endovascular Approach," Part II: Preliminary Clinical Experience, J. Neurosurg. vol. 75, Jul. 1991, pp. 8-14.

(Continued)

*Primary Examiner*—Roy D Gibson
(74) *Attorney, Agent, or Firm*—Blakely Sokoloff Taylor & Zafman LLP

(57) ABSTRACT

An apparatus and method for electrically induced thrombosis. The surgical device includes a first electrode and a second electrode. The first electrode is for placement adjacent to, near, or within a treatment site of a patient. The second electrode can be movable with respect to the first electrode. When the electrodes are charged by an electricity source, negatively charged blood components are attracted to the positively charged electrode while being repelled from the negatively charged electrode. Due to the electric potential between the adjacent electrodes, thrombosis is induced. The negatively charged blood and components form a thrombus or a clot adjacent to the positively charged electrode. The surgical device can be used to induce the otherwise natural process of thrombosis. When the surgical device is used in a treatment site such as a puncture or incision, the thrombosis can seal the opening created by the treatment site.

3 Claims, 5 Drawing Sheets

OTHER PUBLICATIONS

Gugliemi, G. M.D., et al., "Embolization of Intracranial Aneurysms with Detachable Coils and Electrothrombosis," Interventional Neuroradiology Endovascular Therapy of the Central Nervous System, Chapter 5, pp. 63-75.

Hosobuchi, Y., M.D., "Electrothrombosis of Carotoid-Cavernous Fistula," J. Neurosurg., vol. 42., Jan. 1975, pp. 76-85.

Kensy, K., "Groin Management After Coronary Stenting: The Angio-Seal™ Device," Endoluminal Stenting, Chapter 45, pp. 318-324.

Kipshidze, N., "Novel Method of Sealing of Entry Sites Following Endovascular Procedures," Endoluminal Stenting, Chapter 47, pp. 328-331.

Sawyer, P., et al., "Bio-Electric Phenomena as an Etiologic Factor in Intravascular Thrombosis," Navel Medical Research Institute and Tissue Bank, vol. 175, pp. 103-107.

Spokojny, A., et al., "Groin Management After Coronary Stenting: The Vasoseal™ Device," Endoluminal Stenting, Chapter 46, pp. 325-327.

Vetter, J.W., et al., "Groin Management After Coronary Stenting: The Perclose™ Device," Endoluminal Stenting, Chapter 48, pp. 332-337.

* cited by examiner

APPARATUS AND METHOD FOR ELECTRICALLY INDUCED THROMBOSIS

RELATED APPLICATIONS

This is a continuation of application Ser. No. 09/624,924, now abandoned, filed on Jul. 25, 2000.

FIELD OF THE INVENTION

The invention relates generally to an apparatus and method for electrically inducing thrombosis and, more particularly, to the use of electrothrombosis to aid processes including thrombosis, hemostatis, embolization, anastomotic sealing, and void filling at a treatment site of a patient.

BACKGROUND OF THE INVENTION

Various blood vessels and organs can be pierced or cut in connection with numerous surgical procedures or as a result of an accidental trauma. Examples of such surgical procedures include percutaneous transluminal coronary angioplasty (PTCA), angiography, biopsies, anastomosis procedures, as well as various neuro-interventional access procedures. After the surgery is complete or after accidental trauma, the treatment site, e.g., the puncture, cut, or wound, is closed. Surgical methods such as suturing, stapling, or gluing can be used to close the puncture, cut, or wound. In some cases, the treatment site can be closed by natural coagulation and without the aid of sutures, staples, glue, or the like.

Many surgical procedures can be performed using minimally invasive techniques such as those that require catheterization. During catheterization procedures in general, a physician or nurse will create an opening in an artery or other vessel using a conventional catheter introducer or dilator. The artery is accessed through an incision or puncture through the skin and muscle tissue of the patient. Depending upon the type of procedure and the size of the catheter that is used, the size of the opening will vary. Additionally, a further enlargement of the incision or puncture will often occur as the catheter is twisted or otherwise manipulated while being advanced through the body of the patient.

Angiography and angioplasty are examples of surgical procedures that are performed using catheters. Angiography is a diagnostic procedure in which a dye is injected into an artery, such as the femoral artery, to detect coronary disease. PTCA, or angioplasty, is a therapeutic procedure involving the inflation of a balloon in an artery, such as the coronary artery, for the purpose of clearing arterial occlusions. During catheterization, an incision is made in the femoral artery, and a balloon catheter is inserted and fed to the location of the occlusion in the coronary artery. The balloon is inflated and deflated in an attempt to open the occlusion in the artery. Alternatively, a rotational tip catheter may also be used to remove plaque buildup utilizing a technique known as differential cutting. Arterial catheterization procedures are generally performed through a puncture or an incision at the entry point of the catheter which must be closed once the surgery is complete.

One common technique for closing a treatment site such as a puncture after a catheterization procedure has been completed includes applying manual pressure and pressure dressing on the puncture site until the puncture site is sealed by the natural coagulation of blood. Patients undergoing such procedures are often medicated with an anticoagulant such as heparin, thus requiring a nurse to apply external pressure to the puncture site for a lengthy period of time. This procedure may immobilize the patient for an extended period of time, resulting in great inconvenience, pain, anxiety, and discomfort for the patient. Also, additional time is required of the medical personnel and facilities. Furthermore, the pressure application technique may fail to prevent hemorrhage and this may be life-threatening. Moreover, a painful hematoma or bruise may develop at the puncture site because the vessel may continue to bleed internally until clotting blocks the opening in the vessel.

Other techniques for closing a treatment site after a surgical procedure such as catheterization include the use of staples or sutures that can be applied manually or by mechanical devices. One such mechanical device deploys needles through the puncture. The needles have sutures attached, which are subsequently tied to close the treatment site. The sutures can later be removed or can be of the type that dissolve as the healing process progresses.

Another method includes the use of a biocompatible glue that holds the treatment site closed so that the natural process of coagulation and healing can proceed. The biocompatible glue eventually disintegrates as the treatment site heals.

The treatment site closing techniques such as suturing, stapling, or gluing all require additional time to perform the procedures. Also, these techniques introduce foreign material into the body of the patient. Foreign material can increase the chance of infection or inflammatory response. In some cases, the body absorbs the foreign material during the process of disintegrating of the material and healing of the treatment site.

The manual pressure technique generally does not require the use of foreign materials. Relying on natural coagulation of blood to close the treatment site, however, can be time consuming and uncomfortable to the patient. As in any surgical procedure, a less invasive and faster procedure can lessen or minimize patient discomfort.

SUMMARY OF THE INVENTION

The present invention includes a surgical device having a first electrode and a second electrode. The first electrode is an elongated electrode for placement adjacent a treatment site of a patient. The second electrode is adjacent to the first electrode. The first and second electrodes cooperate to electrically induce thrombosis within the treatment site.

DETAILED DESCRIPTION

Figure 1:
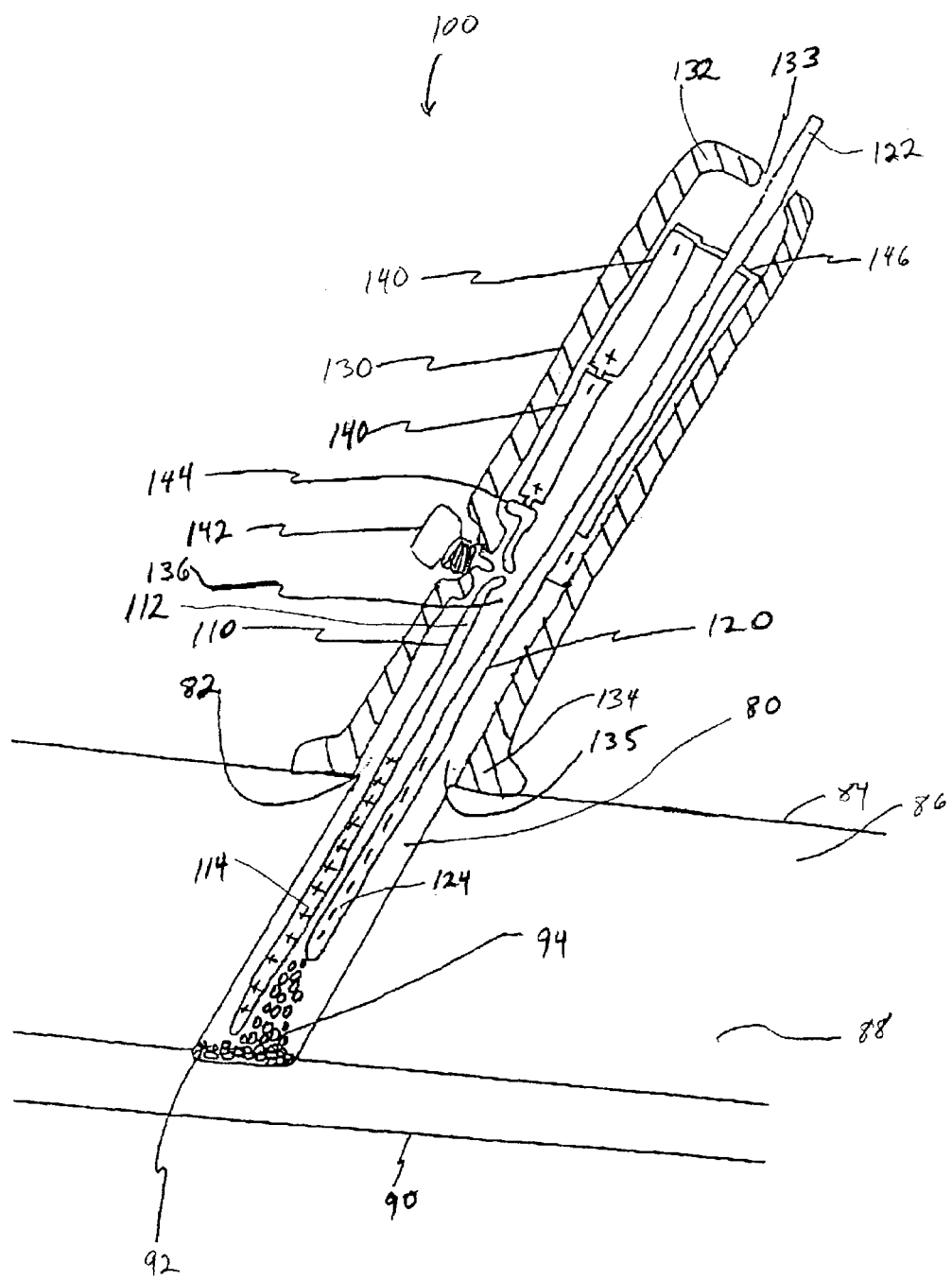
FIG. 1 is cross sectional view of one embodiment of a surgical device for inducing thrombosis in a treatment site of a patient.

Various embodiments of a surgical device are described herein and shown in the drawings. The invention is embodied in an apparatus and method for aiding thrombosis through the application of electric potential at the treatment site of a patient. The apparatus and method can be used to repair a blood vessel, or seal a wound, opening, or puncture at the treatment site in the body of a patient. Clotting of blood (thrombosis) is induced at the treatment site by the application of a first electrode and a second electrode which cooperate to electrically induce thrombosis within the treatment site.

It has been observed that electric potential can be used to induce thrombosis. It is known that white blood cells, red blood cells, fibrinogen, and other protein components of blood are negatively charged. Natural thrombus formations within an artery may be due to abnormal electric potentials in the aortic wall. An aorta includes an outer layer of collagen and elastin that is referred to as the adventitia. The inner layer, or intima, of a blood vessel includes an endothelium which is a layer of flat cells lining the blood vessel. The intima of a normal aorta is polarized negatively with respect to the adventitia. Since the intima and the blood components are all negatively charged, they are physically repelled from each other. When trauma to the intima occurs, however, exposure of the positively charged adventitia attracts negatively charged blood components thereby forming thrombus. This phenomenon can be artificially induced by applying an instrument that carries an electric charge to the components of the blood within a treatment site. It has been observed that the passage of current through blood between a positively charged electrode and a negatively charged electrode will result in thrombosis or clot formation on or near the positively charged electrode.

A surgical device that includes a positive electrode and a negative electrode can be used to seal a treatment site such as an opening made by surgery or trauma. A treatment site can be a puncture or an incision. Upon completion of a surgical procedure, a surgical device such as described herein can be used to close the surgical opening by inserting the electrodes into the treatment site. Sealing is achieved by inducing thrombosis with controlled electric potential between the electrodes.

In a catherization procedure, for example, the treatment site is typically a puncture through the skin and underlying tissue of the patient. The puncture has a depth extending into the patient's body such that access to a blood vessel is provided. To achieve a progression of the electrically induced thrombosis from the depth of the treatment site up to the surface of the body of the patient, one of the electrodes can be retracted up to the surface and can exit the treatment site. While the electrodes are electrically charged, the induced thrombosis will progress along the length of the treatment site to follow the electrode that is being retracted.

The sealing thrombosis can be induced relatively quickly as compared to the technique of applying manual pressure and waiting for natural coagulation of the blood to occur. This is beneficial for patients who have undergone surgery that requires administration of an anticoagulant such as heparin. Thrombosis can be electrically induced relatively quickly even in heparinized blood compared to the technique of applying manual pressure and waiting for the effect of the anticoagulant to wear off so that the blood can coagulate naturally.

FIG. 1 shows one embodiment of a surgical device 100 that can be used for electrically inducing thrombosis in a treatment site 80 of a patient. Treatment site 80 as shown in FIG. 1 is a puncture through body tissue that was made in preparation for a catherization procedure. Treatment site 80 is made to provide access to blood vessel 90. Vessel opening 92 is an incision, puncture, or cut in blood vessel 90 through which a catheter can be inserted. Treatment site 80 is formed by creating a puncture through the skin 84, fascia 86, and perhaps muscle tissue 88. Outer opening 82 is an incision or puncture hole at the surface of the patient's skin 84. After the catherization procedure is complete and the catheter is withdrawn, vessel opening 92 can be closed with sutures, staples, or the like if the opening is about 16 French or greater. If less than 16 French then the opening is not closed.

After the vessel opening 92 is closed if necessary, treatment site 80, which extends through the skin 84, fascia 86, and muscle tissues 88, must also be closed. One technique to close the treatment site 80 is to apply manual pressure and pressure dressing to the area of the body directly above treatment site 80 for a period of time so as to allow natural coagulation of blood that is present within treatment site 80 to occur.

As shown in FIG. 1, surgical device 100 aids in the closure of treatment site 80 by inducing thrombosis within treatment site 80. A thrombus 94 is formed that fills the void created by the puncture that was made to provide access to the blood vessel 90. It should be noted, however, that the apparatus and method described herein can be used to assist in closing other types of treatment sites in a patient's tissue. FIG. 1 shows an exemplary treatment site in the form of a puncture made during a catherization procedure.

Surgical device 100 includes a first elongated electrode 110 for placement into the treatment site 80 of the patient. A second electrode 120 is adjacent to the first electrode 110. The first electrode and the second electrode cooperate to electrically induce thrombosis within the treatment site 80.

The surgical device 100 shown in FIG. 1 includes a housing 130 within which the first electrode 110 and second electrode 120 are assembled. The housing has a proximal end 132 and a distal end 134. The first electrode 110 and the second electrode 120 extend from the distal end 134 of the housing 130. Proximal end 132 can have a proximal opening 133, as shown in FIG. 1. Distal end 134 has a distal opening 135. First electrode 110 and second electrode 120 extend longitudinally through distal opening 135.

In the embodiment shown in FIG. 1, first electrode 110 is fixedly mounted in housing 130. Second electrode 120 is longitudinally movable within the housing 130 with respect to the first electrode 110. Second electrode 120 is elongated and is generally parallel to first electrode 110. First electrode 110 has a proximal end 112 and a distal end 114. Proximal end of first electrode 110 is mounted within housing 130. Distal end 114 extends from distal end 134 of housing 130. Second electrode 120 has a proximal end 122 and a distal end 124. Proximal end 122 can extend from the proximal end 132 of housing 130. In the embodiment of the surgical device 100 in which second electrode 120 is retractable or longitudinally movable within housing 130, proximal end 122 of the second electrode 120 can provide a gripping location for the operator to hold when moving or manipulating second electrode 120 longitudinally through the housing 130. Distal end 124 of the second electrode 120 extends from the distal end 134 of the housing 130. Distal end 124 of the second electrode 120 is generally parallel to and adjacent to distal end 114 of the first electrode 110.

In use, the first electrode 110 and second electrode 120 are inserted into the treatment site 80 through outer opening 82. Preferably, the electrodes are inserted completely into the depth of treatment site 80 so that thrombus 94 formation can be induced throughout the length of the treatment site 80.

Surgical device 100 can also include an electricity source 140. In the embodiment shown in FIG. 1, electricity source 140 is a battery having a positive and negative terminal. FIG. 1 shows two batteries 140 contained within the housing 130. As shown in FIG. 1, the electricity source 140 provides a positive charge to the first electrode 110 and a negative charge to the second electrode 120. Alternatively, the electricity source 140 can provide a negative charge to the first electrode 110 and a positive charge to the second electrode 120. As shown in FIG. 1, electricity source 140 is connected to the first electrode 110 through a first conducting element 144 and a switch 142. Electricity source 140 is also connected to second electrode 120 through second conductive element 146. Second conductive element 146 can be slidably associated with second electrode 120 such that second electrode 120 is movable without becoming electrically disconnected from electricity source 140.

It is not necessary, however, for electricity source 140 to be batteries nor to be contained within housing 130. The surgical device 100 can be provided with a connector for connecting to an external electricity source. Also, switch 142 need not be located on the housing 130 of the surgical device 100. A remote switch such as a foot pedal can be provided for surgical device 100.

In operation, switch 142 is pressed by the operator to electrically connect first conducting element 144 to first electrode 110. A circuit is thus completed such that an electric potential is created through the blood that is between the distal end 114 of first electrode 110 and the distal end 124 of the second electrode 120. An electric current between the electrodes is created because the blood between the respective distal ends of the first and second electrodes is electrically conductive.

Because of the electric potential between the respective distal ends of the first and second electrodes, electrothrombosis is induced within treatment site 80. In the treatment site 80 shown in FIG. 1, the thrombosis can progress upwardly from the vessel opening 92 toward the outer opening 82 of the treatment site 80 by following the retreating second electrode 120 as the second electrode 120 is moved proximally through housing 130 while switch 142 is depressed to complete the electric circuit.

It has been observed that clotting will occur on the positively charged electrode. As the thrombosis progresses, it may be necessary to control the amount of current because the thrombus forming around the positive electrode will act as an insulator between the first and second electrodes. The rate of retraction of the second electrode is preferably selected to allow formation of a thrombus that adequately seals the void within treatment site 80. The potential difference between the first and second electrodes can be monitored during this process such that the rate of removal of the second electrode and the current supply to the electrodes can be controlled to maximize the effect of the electrically induced thrombosis.

The electrodes can be made of an electrically conductive metal such as stainless steel, platinum, or the like. The housing of the surgical device 100 can be made of a durable, sterilizable material such as polycarbonate or ABS. Materials other than those listed also may be used for the housing. First electrode 100 and second electrode 120 can be relatively rigid or, alternatively, can be flexible so as to accommodate treatment sites that may be curved.

Surgical device 100 can include a channel 136 within housing 130. Channel 136 can be provided to hold a biocompatible material, such as fibers or a mixture including biocompatible particles saturated with an electrolytic fluid. The biocompatible material or mixture can be released from within channel 136 and into the treatment site 80. The thrombosis induced within the treatment site 80 can incorporate the biocompatible material that mixes with the blood and assists as a structural matrix. If the biocompatible material is saturated with an electrolytic fluid, this will cause the particles to become polarized and attract negatively charged blood components. An example of a biocompatible mixture that can be used in this manner is particles or fibers of collagen mixed with saline.

FIG. 1 shows one exemplary treatment site 80 in the form of a puncture for a catheterization procedure. Other surgeries or procedures may require different types of openings to be made in the body of the patient. The method and apparatus described herein are adaptable to a variety of types of treatment sites, including, but not limited to, treatment sites described herein. For ease of description, the embodiments of electrodes are describe as being placed adjacent to a treatment site, which is to be understood as encompassing placement within or into a treatment site, as in the above example of treatment site 80, which is a puncture for catheterization.

Figure 2:
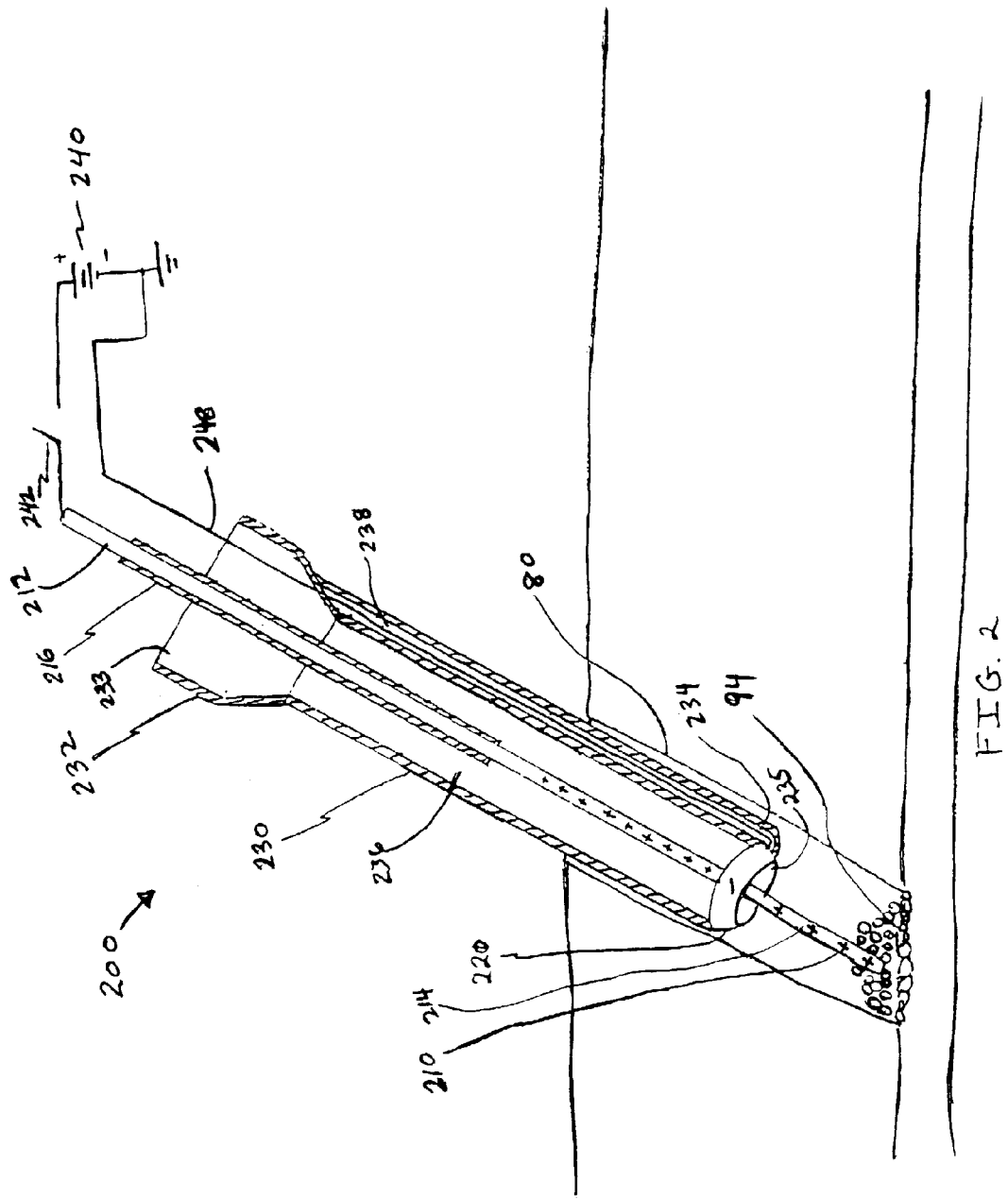
FIG. 2 is a cross sectional view of another embodiment of a surgical device for inducing thrombosis.

FIG. 2 shows another embodiment in which surgical device 200 includes an elongated first electrode 210 and a second electrode 220 which is a ring electrode. Ring electrode 220 is slidably assembled around the first electrode 210. The first electrode 210 is for placement adjacent to a treatment site 80 of a patient. The first electrode 210 and the ring electrode 220 cooperate to electrically induce thrombosis 94 within treatment site 80.

Surgical device 200 includes a housing 230. Housing 230, as shown in FIG. 2, is an elongated, hollow, generally tubular structure having a proximal end 232 and a distal end 234. Proximal end 232 of housing 230 defines a proximal opening 233, and distal end 234 of housing 230 defines a distal opening 235.

Elongated first electrode 210 has a proximal end 212 and a distal end 214. The distal end 234 of housing 230 is associated with the distal end 214 of first electrode 210. Proximal end 212 of first electrode 210 can extend through proximal opening 233 of housing 230.

Alternatively, first electrode 210 can be of a length such that its proximal end 212 does not extend through proximal opening 233. First electrode 210 can be fixed within housing 230 or can be movable longitudinally with respect to housing 230.

Ring electrode 220 is attached to the distal end 234 of housing 230. In the embodiment in which first electrode 210 is longitudinally slidable within housing 230, the surgical device 200 can be inserted into a treatment site 80 such that ring electrode 220 and first electrode 210 are placed at or near the bottom of the puncture formed at treatment site 80. During use, first electrode 210 can be held in place with its distal end 214 at the bottom of treatment site 80 while housing 230 along with ring electrode 220 are retracted upwardly and outwardly from treatment site 80. As the housing 230 is retracted, and while the electrodes are energized, the thrombosis progresses upwardly along first electrode 210 to follow second ring electrode 220 outwardly of the treatment site 80. Once the entire void created by the puncture at treatment site 80 is filled with an electrically induced thrombus, the first electrode 210 can be withdrawn from the patient.

The housing 230 can also define a channel 236 which can hold a biocompatible material such as a collagen-saline mixture. The biocompatible material can be forced out of channel 236 or through channel 236 and out of distal opening 235 into the treatment site 80. Alternatively, a separate conduit (not shown) can be provided through housing 230 or through channel 236 to carry such material.

Surgical device 200 also includes an electricity source 240. In FIG. 2, electricity source 240 is shown as an external or remote electricity source that provides a positive charge to first electrode 210 and a negative charge to ring electrode 220. A switch 242 can be provided between electricity source 240 and first electrode 210. Insulation 216 can be provided around first electrode 210 near its proximal end 212 to electrically isolate first electrode 210 from housing 230. A wiring channel 238 can be provided longitudinally along housing 230 to carry a wire 248 from electricity source 240 to ring electrode 220.

FIGS. 3A through 3D show another embodiment in which a surgical device 300 includes a first electrode 310, a second electrode 320, a housing 330 and a collar 350 slidably assembled around housing 330. FIGS. 3A through 3D also illustrate a method of inducing thrombosis at a treatment site 80 of a patient.

Figures 3A, 3B, 3C, 3D:
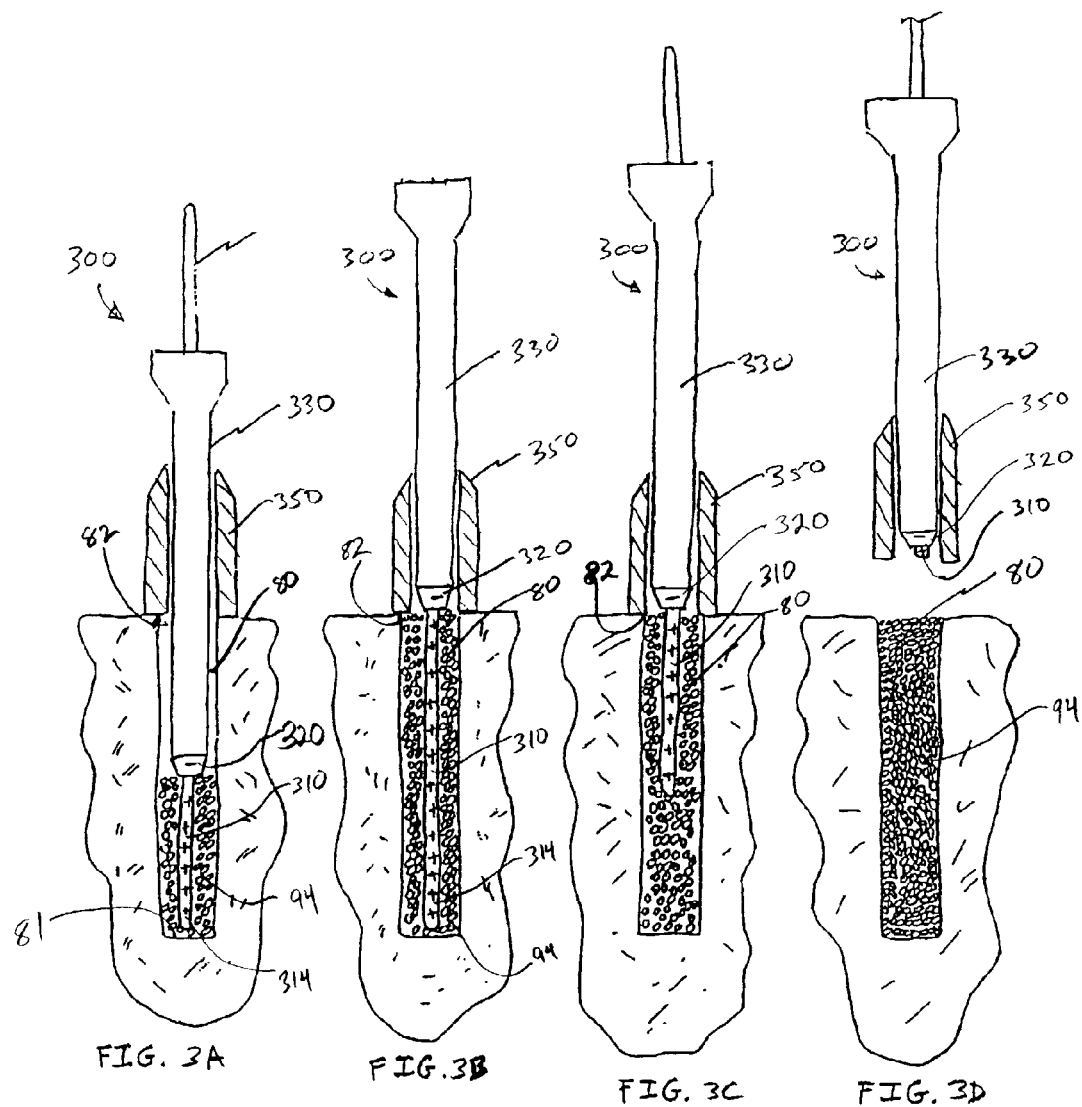
FIGS. 3A through 3D are partial cross sectional views of the surgical device of FIG. 2 showing a method of use of the surgical device.

FIG. 3A shows first electrode 310 placed within treatment site 80 such that the distal end 314 is near the bottom 81 of the void created by a puncture at treatment site 80. For purposes of illustration, first electrode 310 is shown within treatment site 80. In order to induce thrombosis, first electrode 310 and second electrode 320 must be arranged so that electric current can flow between the positively charged first electrode 310 through blood to the negatively charged second electrode 320. The spacing between first electrode 310 and second electrode 320 should be selected such that the negatively charged components of the blood between first electrode 310 and second electrode 320 are attracted to the positively charged first electrode 310 and repelled by negatively charged second electrode 320, thus inducing thrombosis.

FIG. 3A shows second electrode 320 partially withdrawn from treatment site 80. Thrombus 94 has been formed around the distal end 314 of first electrode 310. FIG. 3B shows housing 330 withdrawn from treatment site 80 such that second electrode 320 has been moved to the outer opening 82. Distal end 314 of first electrode 310 is shown remaining fully inserted into treatment site 80 with thrombus 94 surrounding first electrode 310 along the length of treatment site 80. Collar 350 remains against outer opening 82.

Collar 350 is placed against outer opening 82 of treatment site 80 to provide a stabilizing and grasping mechanism to assist in the operation of surgical device 300. As illustrated in FIGS. 3A and 3B, collar 350 can be held against outer opening 82 while housing 330 can be grasped and removed from treatment site 80.

FIG. 3C shows the removal of first electrode 310 from treatment site 80. First electrode 310 is retracted or moved longitudinally through housing 330 while collar 350 remains against outer opening 82. Alternatively the entire device 300 can be moved away from the patient, i.e., out of treatment site 80, without moving first electrode 310 through housing 330.

FIG. 3D shows first electrode 310 fully retracted through housing 330 and surgical device 300 being removed from the treatment site 80. Treatment site 80 has been filled with the electrically induced thrombus 94. The natural healing process can now proceed within treatment site 80. As part of the natural healing process, thrombolysis can occur, which is the breaking up or dissolving of a thrombus. During thrombolysis, naturally occurring compounds in the body encourage the breakup and dissolution of clots.

Figure 4:
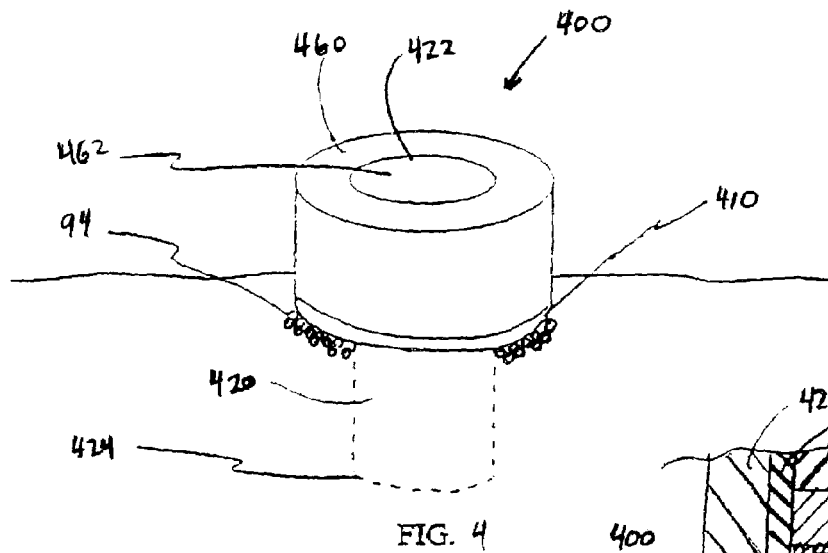
FIG. 4 is a perspective view of another embodiment of a surgical device for inducing thrombosis.

The process of electrothrombosis can also be used to close treatment sites around an access port that is inserted into the treatment site. A trocar for minimally invasive surgery is an example of such an access port that is inserted into an incision. FIG. 4 shows an embodiment of a surgical device 400 that includes a first electrode 410 that is a ring electrode. Surgical device 400 also includes a second electrode 420 that is a tubular electrode having a proximal end 422 and a distal end 424. The ring electrode 410 is mounted coaxially around the tubular electrode 420 between the proximal end 422 and the distal end 424 of the tubular electrode 420. In this exemplary configuration, surgical device 400 is a surgical access port such as a trocar for placement into treatment site of a patient such that the distal end 424 of the tubular electrode 420 extends into the body of the patient, and the ring electrode 410 is adjacent to an outer opening (not shown) of the treatment site (not shown).

The surgical device 400 can also include a collar 460 at the proximal end 422 of the tubular electrode 420. The collar 460 is proximal to the ring electrode 410. Collar 460 has an outer diameter that is larger than the outer opening (not shown) in the tissue of the patient.

Surgical device 400 provides a lumen 462 defined through the tubular electrode 420. Lumen 462 provides access to the interior of the patient's body so that minimally invasive surgical tools, such as catheters or elongated endoscopic tools, can be inserted.

To minimize blood loss from the opening or treatment site, surgical device 400 can electrically induce thrombosis around the circumference of the ring electrode 410. The tube electrode 420 and the ring electrode 410 cooperate to induce thrombosis between the outer opening (not shown) of the treatment site and the ring electrode 410 to seal the treatment site around the circumference of the ring electrode 410. Thrombus 94 is formed around the ring electrode 410.

Figure 5:
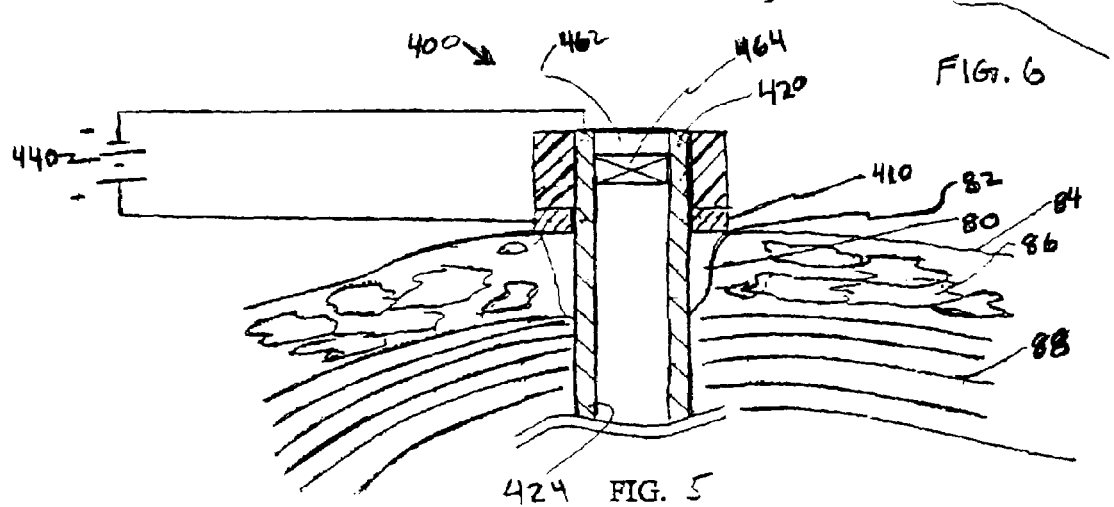
FIG. 5 is a cross sectional view of the embodiment of the surgical device of FIG. 4.

FIG. 5 shows a cross section of the surgical device 400 inserted into the body of the patient through a treatment site 80. Outer opening 82 is at the top of treatment site 80. Ring electrode 410 is shown in contact with outer opening 82. Tubular electrode 420 is shown extending through the skin 84, fascia 86, and muscle tissue 88. Lumen 462 provides access through the length of the tubular electrode 420 into the body of the patient. A valve 464 can be provided within lumen 462 to stop fluid or blood from escaping from the body through lumen 462.

Ring electrode 410 and tubular electrode 420 are connected to an electricity source 440 in a manner similar to previously described embodiments. Because it has been observed that the negatively charged components of blood are attracted to positively charged electrodes, electricity source 440 provides a positive charge to ring electrode 410 and a negative charge to tubular electrode 420. The negative charge provided to tubular electrode 420 repels the negatively charged components of blood within the treatment site 80 at the distal end 424 of the tubular electrode 420. The negative charge repels the negatively charged components of blood so that thrombosis does not occur at the distal end 424 of tubular electrode 420 or within the lumen 462 of the tubular electrode 420.

Figure 6:
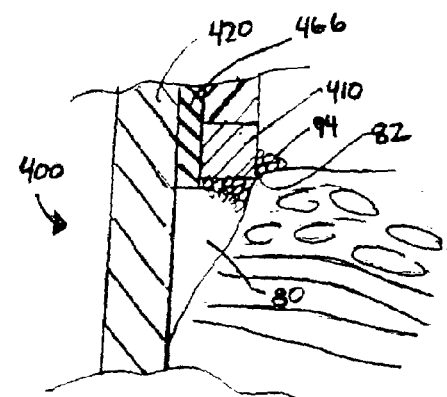
FIG. 6 is an enlarged partial cross sectional view of the surgical device of FIG. 5.

FIGS. 4 through 6 illustrate a surgical device 400 that can be a trocar that provides an access port for minimally invasive surgery or catheterization procedures. Surgical device 400 can also include a housing (not shown) that holds the tubular electrode, the ring electrode, and the electricity source. The electricity source can be carried on the device so that the electrodes can be charged without having wires carrying electricity from an external source.

FIG. 6 shows an enlarged view of a portion of the surgical device 400 of FIG. 5. Ring electrode 410 is shown adjacent to outer opening 82. Insulation 466 is provided between ring electrode 410 and tubular electrode 420 to electrically isolate the electrodes. Ring electrode 410 cooperates with tubular electrode 420 to induce thrombosis between the outer opening of the treatment site 80 and the ring electrode 410. The thrombus 94 created thus seals the treatment site 80 around the circumference of the ring electrode 410.

Figure 7:
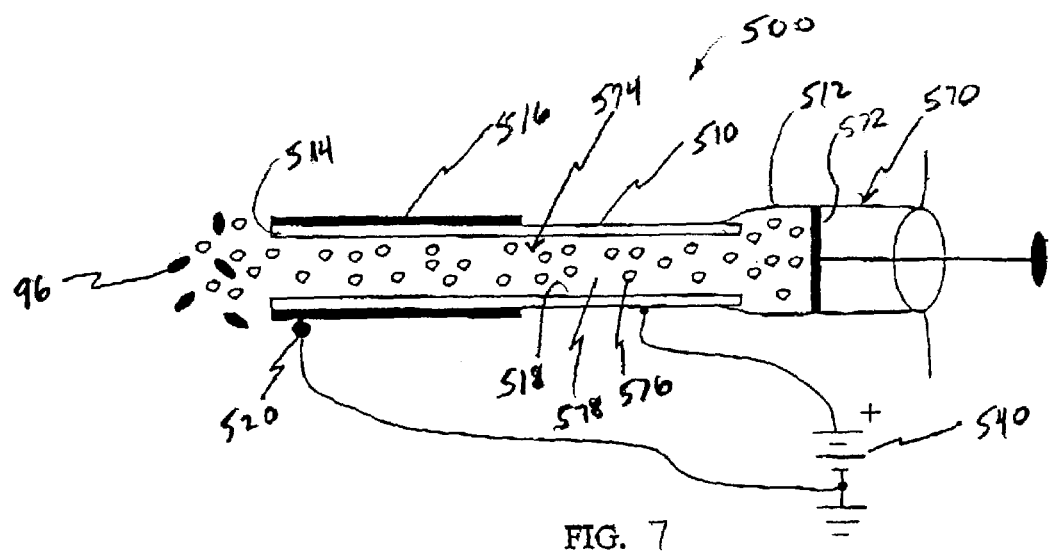
FIG. 7 is a cross sectional view of another embodiment of a surgical device for inducing thrombosis.

FIG. 7 shows an embodiment of a surgical device 500 which includes a first electrode 510 and a second electrode 520. The first electrode is a tube having a proximal end 512 and a distal end 514. The tubular first electrode 510 forms an elongated distal portion of a syringe 570.

The syringe 570 has a plunger mechanism 572 that is slidably inserted into the proximal end 512 of the tubular first electrode 510. Proximal end 512 can be flared outwardly to provide a portion of the syringe 570 with a larger diameter section at the proximal end 512. A biocompatible material 574 can be provided within the syringe 570.

An electricity source 540 provides a positive charge to first electrode 510 and a negative charge to second electrode 520. The electricity source 540 can be carried on the syringe or can be external to the syringe 570, being connected to the electrodes by wires and connectors. The second electrode 520 is mounted near the distal end 514 of the first electrode 510. An insulating layer 516 is provided on the outside of first electrode 510 adjacent to its distal end 514. Insulating layer 516 electrically isolates tubular first electrode 510 from second electrode 520. Insulating layer 516 also provides protection to the patient.

Tubular first electrode 510 defines a lumen 518 through its length. Lumen 518 can carry a biocompatible material 574. The biocompatible material can include a mixture of collagen particles 576 and saline 578, for example. The biocompatible material 574 can be pushed out of the distal end 514 of the tubular electrode 510 by plunger mechanism 572. The biocompatible material 574 is then mixed with the negatively charged components 96 of blood within the treatment site (not shown) of the patient. During use, the first electrode 510 and the second electrode 520 are charged by electricity source 540 and thus cooperate to electrically induce thrombosis.

In use, the biocompatible material 574 is first introduced into the syringe 570. Because the tubular first electrode 510 carries a positive charge from the electricity source 540, the material 574 within the syringe 570 becomes positively electrically charged. The biocompatible material 574 is injected from the syringe 570 into the treatment site of a patient and mixes with blood at the treatment site. The area next to the distal end 514 of the tubular first electrode 510 is positively electrically charged due to the fact that saline is conductive. The blood components 96 necessary for clotting are negatively charged and therefore attracted to the region next to the distal end 514 of the tubular electrode 510. The result is a blood clot-collagen matrix that may be used for aiding the process of thrombosis at the treatment site of a patient.

Figure 8:
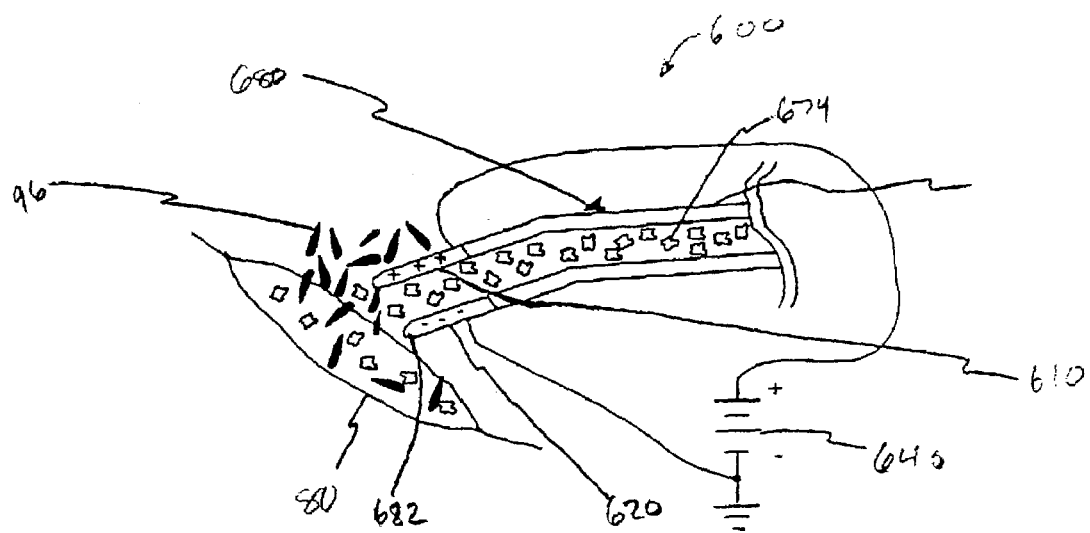
FIG. 8 is a cross sectional view of another embodiment of a surgical device for inducing thrombosis.

FIG. 8 shows another embodiment in which a surgical device 600 includes a nozzle 680 for delivery of a biocompatible material 674. The nozzle 680 has a dispensing end 682. The nozzle 680 also includes a first electrode 610 which is a first conductive portion of the dispensing end 682. The nozzle also includes a second electrode 620 which is a second conductive portion of the dispensing end 682. The first and second conductive portions of the nozzle 680 cooperate to electrically induce thrombosis at a treatment site 80 of the patient.

FIG. 8 also shows an electricity source 640 that provides a positive charge to first electrode 610 and a negative charge to second electrode 620. The electricity source 640 can be carried on the nozzle 680 or can be external to the nozzle, being connected to the electrodes by wires and connectors. The biocompatible material 674 is directed through nozzle 680 and out of dispensing end 682 to be mixed with blood components 96. The result is a blood clot-collagen matrix that aids thrombosis at the treatment site 80.

It should be noted that the embodiments of the method and apparatus described herein are exemplary of the present invention and are not to be construed as limiting the scope of the invention.

What is claimed is:

1. A surgical device comprising;
   a housing having a proximal end and a distal end, the housing having a channel to hold a biocompatible mixture of an electrolytic fluid;
   a ring electrode coupled to the housing;
   an elongated electrode adapted to be longitudinally slidable within the housing, and
   having a proximal portion and a distal portion wherein the distal end of the housing is associated with the distal portion of the elongated electrode; and
   a separate and independent collar slidably assembled around the housing, such that, when the elongated electrode is advanced into an opening of a treatment site within a body of a patient, the collar has a dimension that may be placed against and remain outside of the opening of the treatment site independent of a target depth of the elongated electrode into a patient,
   wherein the elongated electrode and the ring electrode are adapted to cooperate to electrically induce thrombosis within the treatment site.

2. The surgical device of claim 1 wherein the ring electrode is attached to the distal end of the housing.

3. The surgical device of claim 1 wherein the housing further comprises a biocompatible fluid to promote thrombosis within the treatment site.

\* \* \* \* \*